(12) United States Patent
Rosengart

(10) Patent No.: US 6,814,751 B2
(45) Date of Patent: Nov. 9, 2004

(54) METHOD AND APPARATUS FOR PERFORMING AN ANASTAMOSIS

(76) Inventor: Todd K. Rosengart, 1016 Brittany Rd., Highland Park, IL (US) 60035-3952

( * ) Notice: Subject to any disclaimer, the term of this patent is extended or adjusted under 35 U.S.C. 154(b) by 186 days.

(21) Appl. No.: 10/060,958

(22) Filed: Jan. 30, 2002

(65) Prior Publication Data

US 2003/0074057 A1 Apr. 17, 2003

Related U.S. Application Data

(60) Provisional application No. 60/328,731, filed on Oct. 12, 2001.

(51) Int. Cl.$^7$ .................................................. A61F 2/06
(52) U.S. Cl. ........................................................ 623/1.23
(58) Field of Search ................................ 623/1.23, 1.11

(56) References Cited

U.S. PATENT DOCUMENTS

| | | | |
|---|---|---|---|
| 3,946,503 A | | 3/1976 | Buchan et al. |
| 4,909,258 A | * | 3/1990 | Kuntz et al. ............... 600/435 |
| 5,354,276 A | * | 10/1994 | Fonger et al. ......... 604/103.07 |
| 5,456,712 A | | 10/1995 | Magmot |
| 5,484,565 A | | 1/1996 | Larsen et al. |
| 5,522,882 A | | 6/1996 | Gaterud et al. |
| 5,549,553 A | | 8/1996 | Ressemann et al. |
| 5,554,139 A | | 9/1996 | Okajima |
| 5,569,274 A | * | 10/1996 | Rapacki et al. ............. 606/158 |
| 5,575,771 A | | 11/1996 | Walinsky |
| 5,662,614 A | | 9/1997 | Edoga |
| 5,662,675 A | | 9/1997 | Polanskyj Stockert et al. |
| 5,702,412 A | | 12/1997 | Popov et al. |
| 5,718,683 A | | 2/1998 | Ressemann et al. |
| 5,799,282 A | | 8/1998 | Rakshit et al. |
| 5,823,948 A | | 10/1998 | Ross, Jr. et al. |
| 5,830,178 A | | 11/1998 | Jones et al. |
| 5,843,028 A | | 12/1998 | Weaver et al. |
| 5,944,019 A | | 8/1999 | Knudson et al. |
| 5,957,940 A | | 9/1999 | Tanner et al. |
| 5,976,107 A | | 11/1999 | Mertens et al. |
| 5,976,178 A | | 11/1999 | Goldsteen et al. |
| 5,980,484 A | | 11/1999 | Ressemann et al. |
| 5,999,909 A | | 12/1999 | Rakshit et al. |
| 6,001,068 A | | 12/1999 | Uchino et al. |
| 6,014,630 A | | 1/2000 | Jeacock et al. |
| 6,024,748 A | | 2/2000 | Manzo et al. |
| 6,026,814 A | | 2/2000 | LaFontaine et al. |

(List continued on next page.)

FOREIGN PATENT DOCUMENTS

| | | |
|---|---|---|
| GB | 579266 | 7/1946 |
| WO | WO 00/20064 | 4/2000 |
| WO | WO 00/24449 | 5/2000 |
| WO | WO 00/27312 | 5/2000 |

OTHER PUBLICATIONS

U.S. patent application No: 2001–0003985 A1 Published Jun. 21, 2001.

*Primary Examiner*—Eduardo C. Robert
(74) *Attorney, Agent, or Firm*—Kilyk & Bowersox, P.L.L.C.

(57) ABSTRACT

Graft delivery systems and methods for performing a cardiac by-pass procedure using a graft or a mammary artery are described. A combination of catheters and guide devices through the aorta, coronary artery, and the thoracic region can be used to accomplish these procedures.

49 Claims, 9 Drawing Sheets

U.S. PATENT DOCUMENTS

| | | | |
|---|---|---|---|
| 6,027,519 A | 2/2000 | Stanford | |
| 6,030,413 A | 2/2000 | Lazarus | |
| 6,033,378 A | 3/2000 | Lundquist et al. | |
| 6,036,682 A | 3/2000 | Lange et al. | |
| 6,056,719 A | 5/2000 | Mickley | |
| 6,063,114 A | 5/2000 | Nash et al. | |
| 6,068,637 A | 5/2000 | Popov et al. | |
| 6,074,416 A | 6/2000 | Berg et al. | |
| 6,083,234 A | 7/2000 | Nicholas et al. | |
| 6,113,612 A * | 9/2000 | Swanson et al. | 623/1.15 |
| 6,120,432 A | 9/2000 | Sullivan et al. | |
| 6,146,339 A | 11/2000 | Biagtan et al. | |
| 6,146,355 A | 11/2000 | Biggs | |
| 6,149,440 A | 11/2000 | Clark et al. | |
| 6,157,852 A | 12/2000 | Selmon et al. | |
| 6,162,246 A | 12/2000 | Barone | |
| 6,165,139 A | 12/2000 | Damadian | |
| 6,165,140 A | 12/2000 | Ferrera | |
| 6,171,112 B1 | 1/2001 | Clark et al. | |
| 6,186,942 B1 | 2/2001 | Sullivan et al. | |
| 6,196,230 B1 | 3/2001 | Hall et al. | |
| 6,206,849 B1 | 3/2001 | Martin et al. | |
| 6,206,912 B1 | 3/2001 | Goldstein et al. | |
| 6,210,312 B1 | 4/2001 | Nagy | |
| 6,214,016 B1 | 4/2001 | Williams et al. | |
| 6,224,585 B1 | 5/2001 | Pfeiffer | |
| 6,241,667 B1 | 6/2001 | Vetter et al. | |
| 6,253,769 B1 | 7/2001 | LaFontaine et al. | |
| 6,340,441 B1 | 1/2002 | Meyer et al. | |
| 6,508,252 B1 * | 1/2003 | Berg et al. | 128/898 |
| 6,511,491 B2 * | 1/2003 | Grudem et al. | 606/153 |
| 6,533,812 B2 * | 3/2003 | Swanson et al. | 623/1.23 |
| 6,579,311 B1 * | 6/2003 | Makower | 623/1.23 |
| 2002/0108621 A1 | 8/2002 | Berg et al. | |
| 2003/0074007 A1 * | 4/2003 | Rosengart | 606/108 |

* cited by examiner

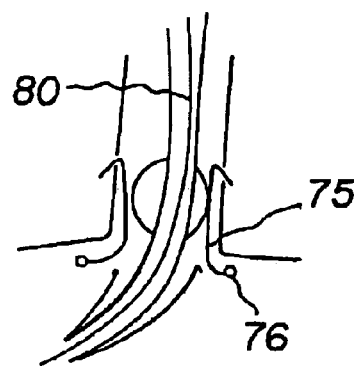
Fig. 6
Fig. 7.1
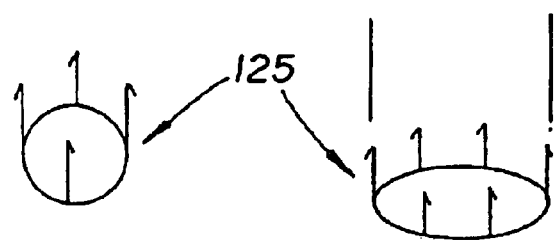
Fig. 7.2    Fig. 7.3

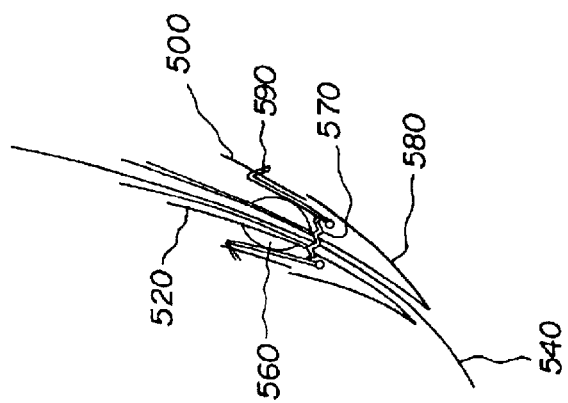
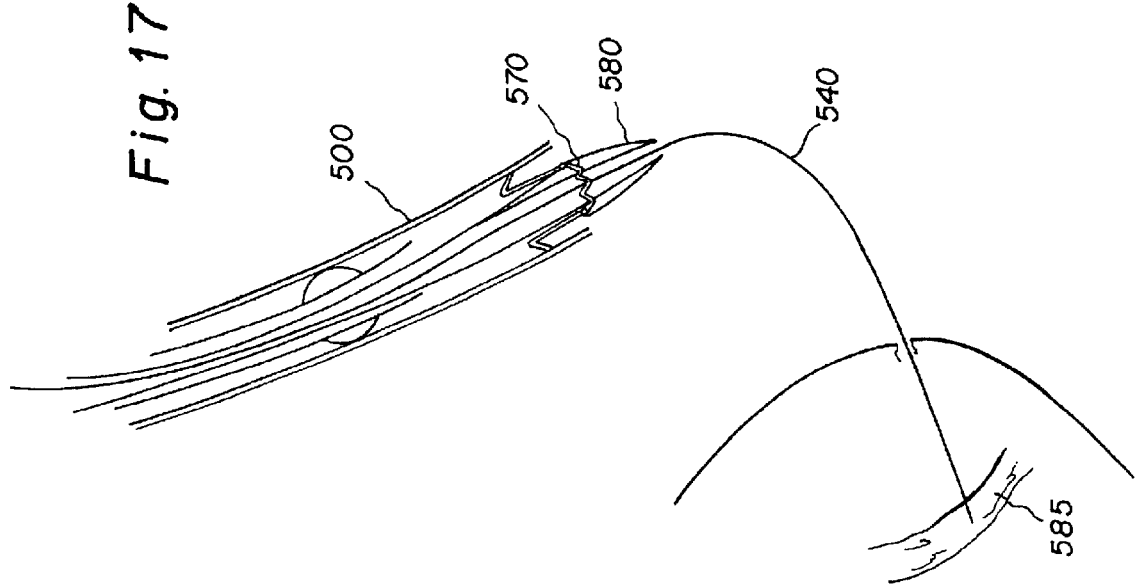

METHOD AND APPARATUS FOR PERFORMING AN ANASTAMOSIS

This application claims the benefit under 35 U.S.C. §119(e) of prior U.S. Provisional Patent Application No. 60/328,731 filed Oct. 12, 2001, which is incorporated in its entirety by reference herein.

BACKGROUND OF PRESENT INVENTION

The present invention relates to an apparatus and a method for performing a cardiac by-pass procedure, also referred to herein as an anastamosis. This invention further relates to grafts for use in the repair, replacement, or supplement of a medical patient's natural body organ structures or tissues. The present invention also relates to methods and apparatus for delivering a graft to an operative site in a patient and for installing the graft at that site.

Several procedures are known for revascularizing the human heart in order to treat a patient with one or more occluded coronary arteries. One of the earliest of these procedures involves exposing the heart by a midline sternotomy. Following surgical exposure of the heart, the patient's aorta and vena cava are connected to a heart/lung machine to sustain vital functions during the procedure. The beating of the heart is stopped to facilitate performance of the procedure. Typically, a suitable blood vessel, such as a length of the patient's saphenous (leg) vein, is harvested for use as a graft. The graft is used to create a new, uninterrupted channel between a blood source, such as the aorta, and the occluded coronary artery or arteries downstream from the arterial occlusion or occlusions. A variation of the above procedure involves relocating a mammary artery of the patient to a coronary artery. Although the above-described sternotomy procedures grow more successful each year, the invasiveness of these procedures, the stopping of the heart, and the necessity for general anesthesia are significant disadvantages. Indeed, these disadvantages preclude the use of sternotomy procedures on many patients.

More recently, less invasive procedures have been developed for revascularizing the heart without using the heart/lung machine ("beating heart" procedures). Two problems with "beating heart" coronary artery repair are the active movement of the beating heart and the challenge of creating anastamoses to the aorta and coronary arteries while they are filled with blood. Various devices and methods have been devised to attempt to immobilize the heart and create a bloodless field to facilitate such beating heart procedures. Drugs may be administered to the patient to slow the heart during the procedure, stabilizing devices may be placed on the surface of the heart, and shunts or snares may be introduced into or around the coronary arteries to allow stabilization of the coronary arteries and construction of the coronary anastamoses in a bloodless field.

A less invasive method for revascularizing the human heart involves gaining access to the thoracic cavity by making incisions between the patient's ribs. This procedure is known as a thoracotomy. A thoracotomy procedure is substantially less traumatic than a midline sternotomy, but it is still too traumatic for some patients. An even less invasive procedure is known as thoracostomy, which involves the surgical creation of ports in the patient's chest to obtain access to the thoracic cavity. Specially designed instruments can be inserted through the ports to allow the surgeon to revascularize the heart without causing more significant trauma from a midline sternotomy. Thoracostomy bypass procedures are less traumatic than sternotomy bypass procedures, but the introduction of stabilization devices through thorocostomy ports is cumbersome, impractical, and of limited utility. Furthermore, bypasses to the coronary arteries that are located on dependent portions of the heart are not readily possible with this technique. Several patents have recently been filed or issued in the field of graft and stent assemblies and methods for use thereof. Of particular interest are the following U.S. Pat. Nos. 5,702,412; 5,944,019; 5,976,178; 6,026,814; 6,063,114; 6,068,637; 6,074,416; 6,120,432; 6,186,942; 6,196,230; 6,206,912; 6,253,769; 5,456,712; 5,522,882; and U.S. patent application 2001-0003985 A1. All patents, applications, and publications mentioned here and throughout the application are incorporated in their entirety by reference herein and form a part of the present application.

Accordingly, there is a need for a new improved method and apparatus for performing an anastamosis.

SUMMARY OF PRESENT INVENTION

The present invention relates to a graft delivery system, which includes a first elongated instrument that is insertable into a patient's vascular system. The first elongated instrument preferably includes an aortic catheter and an aortic guide device, preferably an aortic guide wire. The aortic guide device is preferably capable of navigating the aortic catheter to the patient's aorta at a pre-determined location and may be capable of protruding outside of the aorta.

The present invention also includes a second elongated instrument that is insertable into the patient's vascular system. The second elongated instrument preferably includes a coronary catheter and a coronary guide device that is capable of navigating the coronary catheter to a coronary artery of the patient at a pre-determined location. In the preferred embodiment, the coronary guide device is a coronary guide wire.

The present invention also includes a retrieving device, capable of retrieving the aortic guide device and the coronary guide device. Additionally, the retrieving device is capable of extracting the aortic guide device and the coronary guide device through a thoracic aperture in the patient.

Furthermore, the present invention includes a third elongated instrument that is insertable from the exterior of the patient's thoracic region into the patient through the thoracic aperture. This third elongated instrument is navigated by the coronary guide device. Preferably, the third elongated instrument is within a graft that is to be used, for instance, in the by-pass procedure.

Also, the present invention relates to a method for installing a graft that includes (a) inserting a first elongated instrument into the patient's vascular system; (b) navigating the first elongated instrument to a pre-determined location in the aorta of the patient; (c) protruding the aortic guide device from the aorta, thereby creating an aorta aperture; (d) inserting the second elongated instrument into the patient's vascular system; (e) navigating a second elongated instrument to a predetermined location in the coronary artery of the patient; (f) protruding the coronary guide device to the outside of the coronary artery, thereby creating a coronary aperture; (g) creating a thoracic aperture in thoracic region of the patient; (h) retrieving the aortic guide device and extracting the distal end of the aortic guide device and retrieving the coronary guide device and extracting the distal end of the coronary guide device with the retrieving device from the thoracic region of the patient to outside of the thoracic region of the patient; (i) inserting the third elongated instrument through the thoracic aperture, wherein the third elongated instrument is within the graft, and the coronary guide device is threaded through the third elongated instrument to provide a navigation path for the third elongated instrument to the coronary aperture; (j) navigating the third elongated instrument with the graft to the coronary aperture; (k) attaching the distal end of the graft to the coronary aperture to make a fluid tight connection; (l) inserting the distal end of the aortic catheter into the proximal end of the graft and navigating the proximal end of the graft to the aorta aperture; and (m) attaching the proximal end of the graft to the aorta aperture to make a fluid tight connection.

The present invention also relates to graft delivery systems and methods of installing a graft using a mammary artery or similar pathway.

It is to be understood that both the foregoing general description and the following detailed description are exemplary and explanatory only and are intended to provide further explanation of the present invention, as claimed.

BRIEF DESCRIPTION OF DRAWINGS

The foregoing features of this invention will be more readily understood by reference to the following detailed description, taken with reference to the accompanying drawings, in which:

FIG. 6 is a schematic diagram of a thoracic catheter within the graft and a coupler attachable to the coronary artery and the graft;

FIGS. 7.1, 7.2, and 7.3 are schematic diagrams of the coupler as compressed in the conical-shaped device and the coupler after its release from the conical device;

FIG. 17 is a schematic diagram illustrating one method of delivering a coupler attached to the severed end of the mammary artery to the coronary artery.

FIG. 18 is a schematic diagram illustrating the appendages of the coupler that are deployed and are piercing the mammary artery.

DETAILED DESCRIPTION OF PRESENT INVENTION

The present invention relates to a graft delivery system that includes a first elongated instrument that is insertable into a patient's vascular system. The first elongated instrument preferably includes an aortic catheter and an aortic guide device. The aortic guide device is preferably an aortic guide wire. The aortic guide device is preferably a device capable of navigating the aortic catheter to the patient's aorta at a pre-determined location and optionally is capable of protruding outside of the aorta. The present invention may also include a second elongated instrument that is insertable into the patient's vascular system. The second elongated instrument preferably includes a coronary catheter and a coronary guide device that is capable of navigating the coronary catheter to a coronary artery at a pre-determined location. In the preferred embodiment, the coronary guide device is a coronary guide wire. The aorta guide device and the coronary guide device are generally of the same type of construction.

The present invention may also include a steerable retrieving device capable of retrieving the aortic guide device and the coronary guide device. Additionally, the retrieving device is capable of extracting the aortic guide device and the coronary guide device through the thoracic aperture in the patient. Furthermore, the present invention may include a third elongated instrument that is insertable from the exterior of the patient's thoracic region into the patient through the thoracic aperture. This third elongated instrument is preferably navigated by the coronary guide device. Preferably, the third elongated instrument is inserted in the graft to be used in the by-pass procedure. The third elongated instrument preferably includes or is a thoracic catheter that is insertable through a thoracic aperture.

In one example, the first and/or second elongated instruments or parts thereof, such as the coronary catheter can be inserted through the femoral or other peripheral artery. An airtight seal around the thoracic aperture's entry can be used to facilitate continued normal ventilation of the patient. The thoracic aperture's entry is preferably only as large as necessary to accommodate the third elongated instrument. More preferably, the thoracic aperture entry can be approximately equal to the largest of the diameters of the third elongated instrument, fiber optic light/camera system, a docking device, one end of the aortic guide wire and/or aortic catheter, and/or one end of the coronary guide wire. In the present invention, the most preferred diameter of the thoracic aperture is from about 5 mm in diameter to about 10 mm in diameter, though other diameters can be used.

Figure 1:
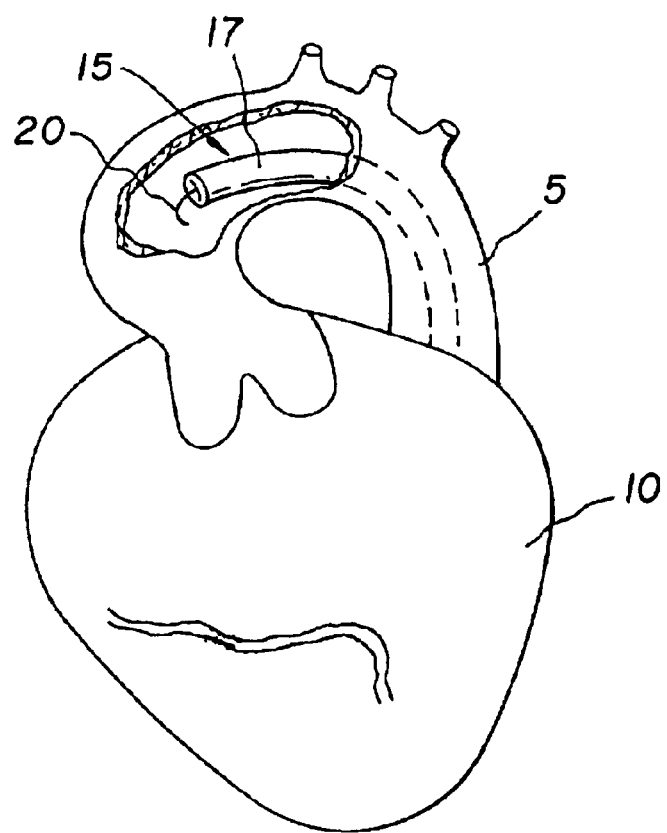
FIG. 1 is a schematic diagram showing the heart, the aorta, and the first elongated instrument having the aortic catheter and the aortic guide wire, of an embodiment of the present invention.

With reference to the figures, the present invention includes first elongated instrument 15, FIG. 1, inserted into a patient's vascular system. First elongated instrument 15 may include aortic catheter 17 and aortic guide device 20 that can be advanced towards heart 10 and into and within the aorta to a desired position. In the preferred embodiment, aortic guide device 20 is an aortic guide wire. The catheters and guide devices can be commercially available tools. The reference to "aortic" for aortic catheter is to better explain the location of use of the catheter and the size and shape requirements that would preferably be used in view of its location of use. This would be true to the other terms preceding "guide wire" and "catheter" and the like.

Figure 2:
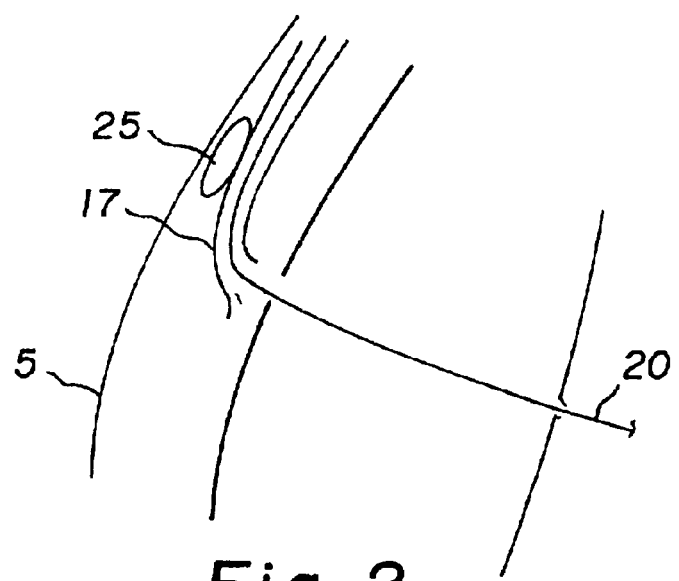
FIG. 2 is a detailed schematic diagram of the first elongated instrument.

In the present invention, aortic guide device 20 can include a sharp end to perforate aorta 5 and to protrude outside of aorta 5. In the preferred embodiment, aortic guide device 20 is an aortic guide wire. Furthermore, first elongated instrument 15 may include at least one aortic stabilizer 25, FIG. 2, to place and hold the instrument in a predetermined location. Aortic stabilizer 25 may be or include a retractable pin(s), a barb(s), a balloon(s), or any combination thereof, and may be located at the distal end of the aortic catheter. In the preferred embodiment of the present invention, aortic catheter 17 may have a hollow distal chamber, similar to a pill-shaped form, which can occlusively be pushed or pulled up against the internal wall of aorta 5 in the manner such that an aperture can be created in the wall of aorta 5 for deployment of aortic guide device 20 and/or aortic catheter 17. In the preferred embodiment of the present invention, aortic catheter 17 also includes a balloon at its end.

Figure 3:
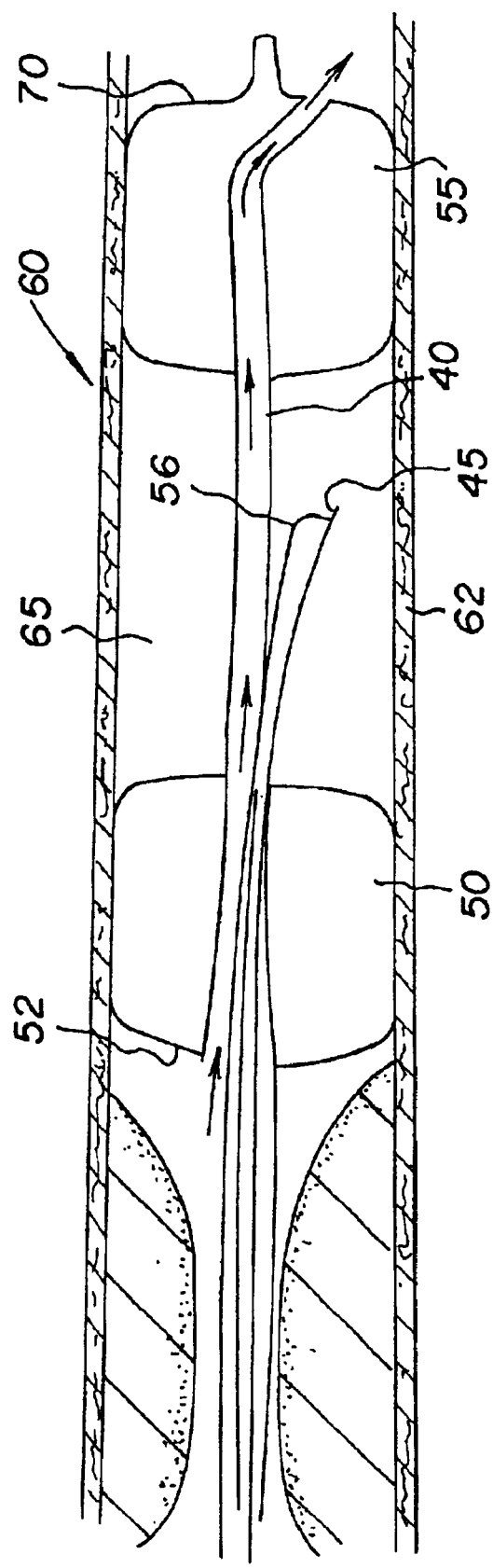
FIG. 3 is a cross-sectional schematic diagram of one embodiment of the second elongated instrument, which includes two hemostatic objects, a shaped perforating guide wire, and a flange.

The second elongated instrument that is insertable into the patient's vascular system includes a coronary catheter and a coronary guide device. The coronary guide device, which is preferably a flexible coronary guide wire is directed towards the coronary artery to preferably perforate the coronary artery at a predetermined location and can protrude outside of the coronary artery. The coronary guide device may include at least one radio-opaque marker to determine its location within the coronary artery. The second elongated instrument may optionally include at least one hemostatic object 50, FIG. 3, to block blood flow. Hemostatic object 50 is preferably a balloon. Hemostatic object 50 may include a first channel that prevents blood flow blockage by directing the blood flow from one side of the hemostatic object to the second side of the hemostatic object. The guide device can perforate the coronary artery or be used to guide an aperture-creating device.

In the preferred embodiment of the present invention, hemostatic object 50 may include a perforating guide device 45 in a second channel. This perforating guide device 45 is preferably used to perforate coronary artery 62 at a predetermined location and can protrude outside of coronary artery 62. Preferably, the coronary guide device is used to direct the second elongated instrument to coronary artery 62. The coronary guide device may include at least one radio-opaque marker to determine its location within the coronary artery. Perforating guide device 45, which preferably is a T-shaped perforating guide wire, can be aligned after the second channel is correctly oriented. The orientation of the second channel can in turn be determined by verifying the orientation of the appropriate radio-opaque markers on the coronary catheter. This orientation is maintained to ensure proper orientation of a dilator.

Perforating guide device 45 can be flexible with a sharp end to perforate the coronary artery. In the preferred embodiment of the present invention, second elongated instrument 60 may also include a 60–90 degree (or any angle) flange 56 to direct T-shaped perforating guide device 45 towards the coronary artery wall to perforate the coronary artery.

More preferably, second elongated instrument 60 also includes second hemostatic object 55 positioned, with respect to hemostatic object 50, to form hemostatic chamber 65 within the coronary artery. First hemostatic object 50 and second hemostatic object 55 of the preferred embodiment include first channel 40 that extends between first hemostatic object 50 and second hemostatic object 55. In the preferred embodiment of the present invention, first hemostatic object 50 and second hemostatic object 55 are balloons. First channel 40 directs the blood flow from side 52 of first hemostatic object 50 blocking the blood flow to side 70 of second hemostatic object 55.

The coronary guide device can have two hemostatic objects 50 and 55, first channel 40, T-shaped perforating guide device 45 and 60 to 90 degree flange 56 at the end of T-shaped perforating guide device or a similarly shaped device. The T-shaped perforating device ensures that a dilator, as will later be described, is properly oriented by using an adaptor on the dilator end designed to receive T-shaped perforating guide device 45 to prevent undesired perforation of coronary artery 62 in an improper orientation.

Second elongated instrument 60 may advance over the coronary guide device within the vascular system to a site, preferably within the distal coronary artery of adequate diameter with minimal atherosclerotic disease, and beyond the coronary occlusion or stenosis, where at hemostatic balloons 50 and 55 may be inflated to contact the inner side walls of the coronary artery and seal the blood flow. In this example, first channel 40 conducts coronary blood flow from side 52 of hemostatic object 50 to side 70 of hemostatic object 55. T-shaped perforating guide device 45 may then be advanced through the second channel and can be directed at a near perpendicular angle by retractable or permanently positioned flange 56 such that T-shaped perforating guide wire 45 punctures the external coronary artery sidewall at a position approximately midway in chamber 65 created by hemostatic object 50 and hemostatic object 55.

Figure 4:
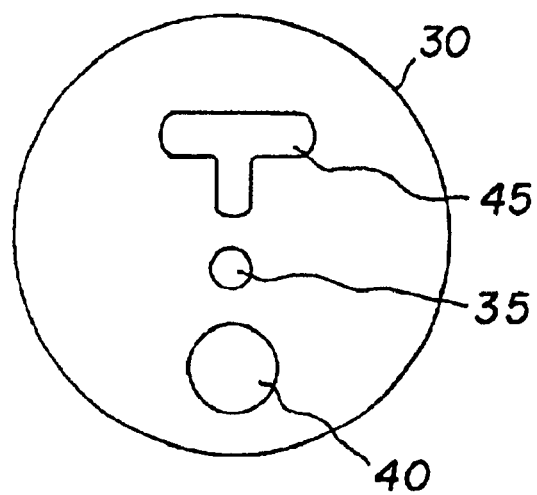
FIG. 4 is a cross-sectional schematic diagram of the second elongated instrument according to one embodiment of the present invention.

FIG. 4 is a cross-sectional schematic of one example of a second elongated instrument illustrating second elongated instrument 30, T-shaped perforating guide 45, coronary guide wire 35 (which guides the second elongated instrument to the coronary artery) and first channel 40.

Figure 5:
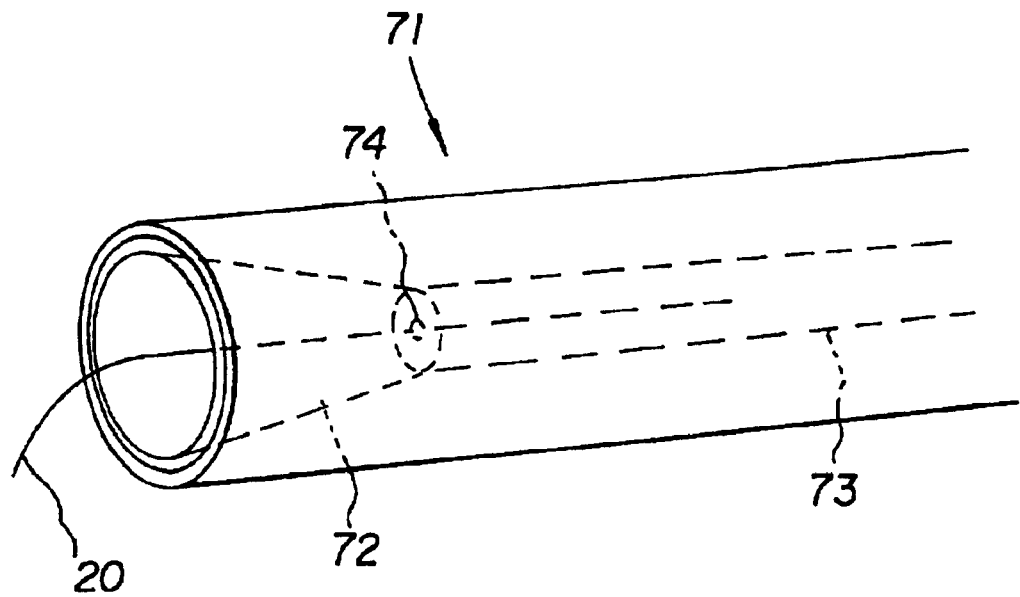
FIG. 5 is a schematic diagram of the retrieving device.

Retrieving device 71, FIG. 5, which is steerable and which receives, secures, and exteriorizes the terminating end of the aortic guide device and the coronary guide device, or preferably T-shaped perforating guide device is advanced into the thoracic region of the patient to make contact with and secure to the terminating end of the guide devices. Retrieving device 71, can include retractable pins and/or hooks that are able to secure the terminating end of the guide devices, bio-compatible adhesive or sealant that are able to achieve or provide temporary adhesion of the guide devices, or magnetically, electrically or otherwise attaching devices. In the preferred embodiment, retrieving device 71 and the end of the guide devices can be magnetized or be adapted to possess opposite polarities to improve the connecting ability of the two components.

For example, a positively charged (magnetized) aortic guide device end is attracted to and can engage a negatively charged retrieving device 71, and a negatively charged aortic guide device end is attracted to and can engage a positively charged retrieving device 71. In the preferred embodiment, the end of retrieving device 71 is conical in shape to form a docking cone 72, with a wide opening at its end. Therefore, the aortic guide device and the coronary guide device can readily contact and secure docking cone 72. Aortic guide device 20 penetrates the face of retrieving device 71, such as a docking cone 72, and cylindrical wall 73 of retrieving device 71 guides aortic guide device 20 as it is further inserted into and secured to the retrieving device. Preferably, aortic guide device 20 is passed through apical aperture 74 in docking cone 72 and passed externally through the thoracic aperture. In a preferred embodiment, the positive or negative charge resides in apical aperture 74 so as to appropriately attract the guide device to the apex of the cone. Retrieving device 71 can then be withdrawn, retaining the aortic guide device externally.

The same process can be repeated for the coronary guide device. In the preferred embodiment, the guide devices are located under video and/or fluoroscopic guidance. In the preferred embodiment, capture of the coronary guide device or preferably the T-shaped perforating guide device may be facilitated by inflation of a balloon near the terminus of this device, which will serve to "suspend" the tip of the coronary guide device or preferably the T-shaped perforating guide device within the pericardial space.

Figure 8:
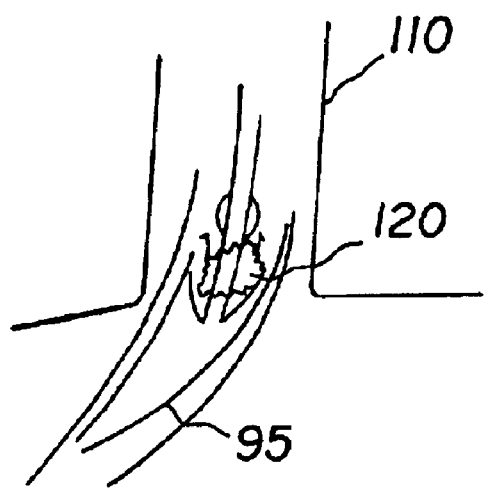
FIG. 8 is a schematic diagram of the thoracic catheter with the coupler positioned in the conical-shaped device.

The third elongated instrument preferably is or includes thoracic catheter 80, FIG. 6 and is inserted within the graft. A coupler is preferably placed on each end of the graft. This coupler can be at least one prong, at least one staple, at least one pin, at least one barb, or any combination thereof. One example of such coupler is coupler 75. Coupler 75 may be deformable, may contain biocompatible sealants, and/or may include at least one sharp prong. In the preferred embodiment, the prongs or distal end 76 of coupler 75 attaching to the coronary artery and to the aorta, for instance, expand to an external diameter of 5 to 10 mm. Other sizes can be used. More preferably, coupler 75 may include a ring of fine wire or other material that can be compressed in a spring-like manner. First coupler 75 is most preferably a compressible ring. Ring 120, FIG. 7.1, expands within the lumen and conforms to the internal geometry of the vessel upon its release from a conical-shaped device and is shown at 125, FIGS. 7.2 and 7.3. A conical-shaped device can be any device that includes reduced or tapered ends and that can enter into an artery or the aorta. In one embodiment of the present invention, the coupler at each end of the graft can be deformable, and preferably made of Nitinol or stainless steel, polyimide, other super-elastic alloys, and the like. More preferably, the coupler at each end of the graft includes a ring that connects to the graft by means of arms of distensible wire to which are attached barbs or other means of penetrating the graft wall. Ring 120, FIG. 8, preferably is within conical-shaped device 95, which is located at each end of the graft 110. In the present invention, it is preferable to compress ring 120 into conical-shaped device 95 at the exterior of the patient's thoracic region. In one example, conical-shaped device 95 may be integrated into each end of graft 110 and a ring, fine wire or other material can be compressed in conical-shaped device 95.

Figure 9:
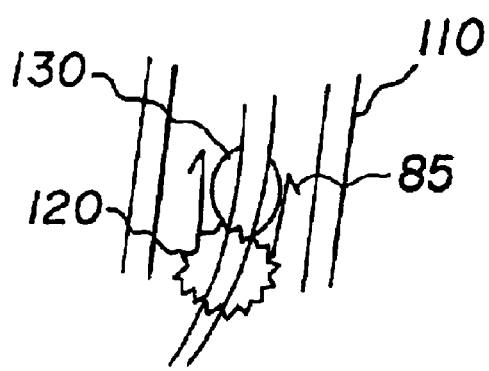
FIG. 9 is a schematic diagram of the position of the graft with respect to the sheath and the coupler.

Ring 120, FIG. 9, may connect to the graft by means of arms of distensible wire to which are attached sharp, downward-directed or otherwise barbed, flexible appendages as shown at 85, FIG. 9. The appendages may include prongs, staples, pins, metallic or plastic bars, or a combination thereof.

The graft material of the present invention is preferably a length of saphenous vein or mammary artery (IMA) on the exterior or the interior of the thoracic catheter. Other graft material can be used such as artificial grafts and the like. Preferably, appendage 85 couples to graft 110 by hemostatic object 130 that can also act as a forcing instrument. Hemostatic object 130 may be a balloon, spring, or a combination thereof. More preferably, hemostatic object 130 is a balloon.

Figure 10:
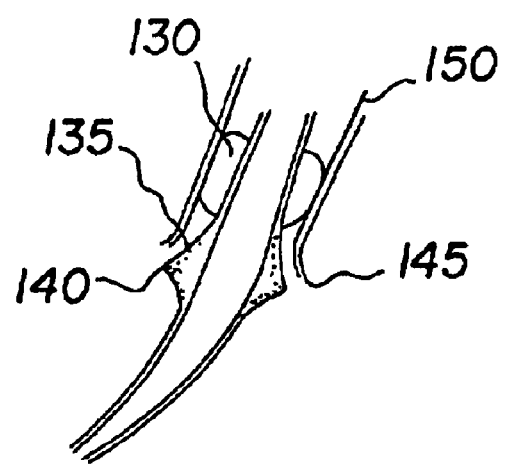
FIG. 10 is a schematic diagram of the concave curvature and the step-off of the third elongated instrument.

In the preferred embodiment of the present invention, the thoracic catheter of the third elongated instrument may include hemostatic object 130, FIG. 10, sheath 150, concave curvature 135 to evert graft edge 145 outwards, and a step-off 140 to limit the advancement of a dilator.

Figure 11:
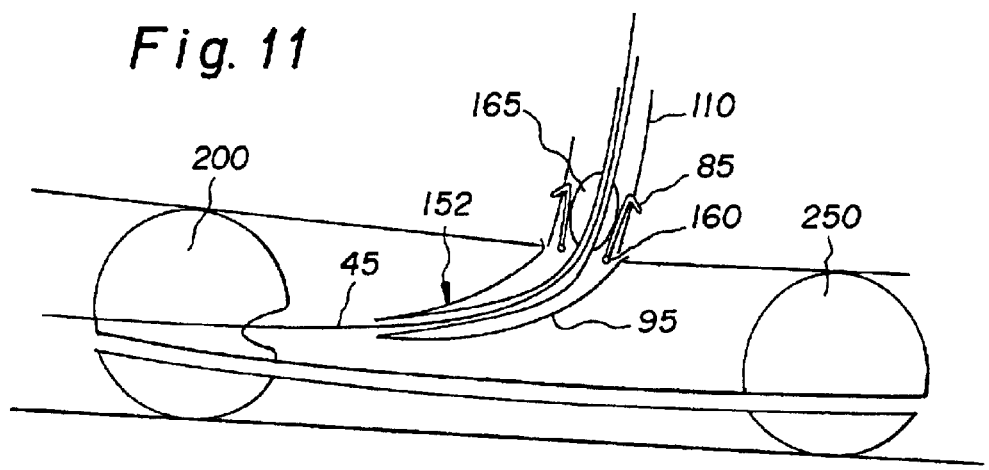
FIG. 11 is a schematic diagram of the conical-shaped device within the lumen of the coronary artery and the two hemostatic objects of the second elongated instrument.

Enlarging instrument 152, FIG. 11, is preferably located within the distal end of graft 110, and more preferably at the distal end of conical-shaped device 95. In the most preferred embodiment, enlarging instrument 152 is located at the end of conical-shaped device 95, wherein conical-shaped device 95 includes a 90 degree or other angle. However, enlarging instrument 152 can be located anywhere so long as it is capable of creating a circular arteriotomy into which conical-shaped device 95 can be inserted. In one embodiment of the present invention, enlarging instrument 152 can be a dilator or a cutter, and the dilator may be passed over the coronary or aortic guide device prior to passage of the thoracic catheter and graft.

Dilator/cutter 152 may open tissue external to the coronary artery or aorta to exceed the external diameter of the graft material so that this extraneous tissue does not impinge on the anastamosis. The edge of dilator/cutter 152 may be beveled to form a sharp edge. Dilator 152 can be adapted to have a groove or a receiving site for the T-shaped perforating guiding device to assure proper orientation of the dilator/cutter. The advancement of the dilator/cutter may be limited by hemostatic object 200 acting as a "stopper" or by the dimensions of the aortic catheter and/or the diameter of the step-off.

In one embodiment of the present invention, dilator/cutter 152 can be tapered so that the coronary or aortic aperture is substantially less than the external diameter of graft 110. Dilator 152 may be configured with a tapered circular tip expanding to a diameter of approximately 3 mm at a distance equal to approximately one-half the distance between hemostatic objects 200 and 250, such that a circular aperture is created in the coronary artery at a point halfway between hemostatic objects 200 and 250.

In the present invention, the coronary aperture is preferably of a pre-determined size created by the diameter of dilator 152. In an embodiment wherein a dilator is passed prior to passage of the thoracic catheter, the dilator could widen to dimensions of approximately 8 mm long by 5 mm wide for a distance of approximately 1 cm beyond its 3 mm diameter coronary aperture point so that epicardial fat or overlying muscle can be effectively cleared from a position overlying the coronary, thereby avoiding the potentially deleterious incorporation of these tissues in the coronary anastamosis. The size of the dilator/cutter can vary based on the diameter of the target artery and/or the planned cross-sectional area of the anastamotic device.

An aortic dilator may be circular or of other configurations and is from about 2 mm to about 8 mm, such that the size of the aperture created is smaller than that of the graft and the expanded aortic anastamotic mechanism. This aperture, as with the coronary aperture, may be post-dilated with larger dilators after completion of the anastamosis to accommodate the size of the graft.

Marker 160, which is preferably a radio-opaque marker, can be placed within graft 110 to detect the position of graft 110. Hemostatic object 165 can be the forcing instrument that attaches appendage 85 of the coupler to graft 110, or appendage 85 may passively fix to the graft after removal of the sheath. Furthermore, the third elongated instrument, which is preferably a thoracic catheter, may include a fiber optic light/camera system. However, the light/camera system may also be in a separate elongated instrument.

The apparatus discussed above can also be used for performing an anastamosis using a mammary artery. The preferred method of performing anastamosis using a mammary artery is described later.

Figure 12:
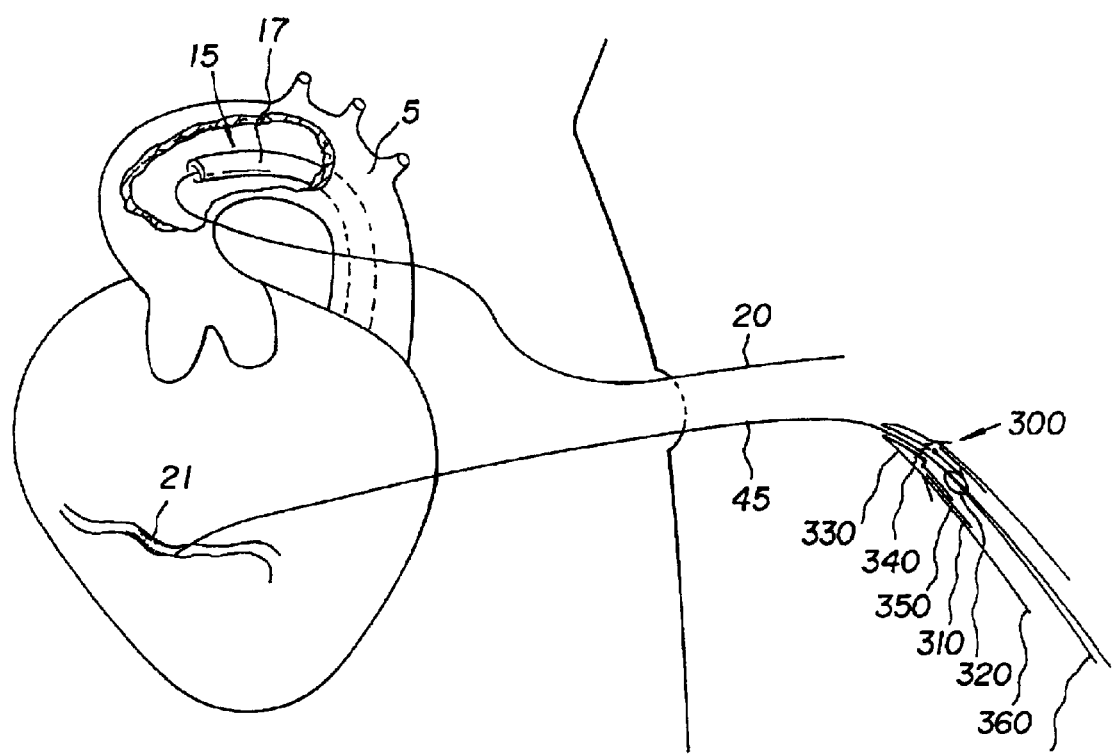
FIG. 12 is a schematic diagram illustrating the approach of the third elongated instrument with the coupler and the conical-shaped device towards the coronary artery.

In a preferred method of the present invention, first elongated instrument 15, FIG. 12, can be inserted into aorta 5. The first elongated instrument 15 preferably includes aortic catheter 17 and aortic guide device 20. Aortic guide device 20 with or without aortic catheter 17, can be capable of creating an aperture through the aorta wall. Essentially, aortic guide device 20 is preferably used to navigate to the desired location of the aorta wall for purposes of creating the aperture. Aortic guide device 20 can be used to initiate the aperture at a desired location in the aortic wall. The creation of the aperture can be done, for instance, by mechanical means or light energy means. The aperture permits first elongated instrument 15 and/or aortic guide device 20 to protrude through the aperture. First elongated instrument 15 and/or aortic guide device 20 can be introduced through peripheral artery and preferably through the femoral artery of a patient located in the leg of a patient.

The second elongated instrument (e.g., the coronary catheter with coronary guide device) can also be introduced through the femoral artery of a patient and along the aortic passage. This second elongated instrument passes the location of the aperture created by first elongated instrument 15 and/or aortic guide device 20 and further passes through any existing blockage, e.g. blockage 21, FIG. 12. Once past blockage 21 (in other words, below the blockage), the coronary guide device, or more preferably T-shaped perforating guide device 45, can be used to create an aperture below the blockage. In the preferred embodiment, T-shaped perforating guide wire 45 protrudes through the coronary artery.

Upon the creation of the first and second apertures, an aperture is then created in the thoracic region of the patient (in other words, the chest of the patient.) At this point, a steerable retrieving device is introduced through the aperture in the thoracic region of the patient. This device retrieves the guide wires and/or the aortic catheter, which are protruding through the aorta aperture and the coronary aperture. The retrieving device can retrieve the guide wires and/or the aortic catheter by mechanical methods, magnetic methods, or other attachment methods that are capable of grabbing the guide devices and/or the aortic catheter at each aperture location. For instance, the device with the necessary retrieving means can first go and retrieve aortic guide device 20 and/or aortic catheter 17 protruding from the aorta aperture. The retrieving device then preferably navigates aortic guide device 20 and/or aortic catheter 17 to the exterior of the patient through the aperture created in the thoracic region. In the same manner, the coronary guide device (or T-shaped perforating guide device 45) protruding from the coronary aperture can be retrieved and also brought to the outside of the patient through the aperture created in the thoracic region. Thus, the distal ends of both guide devices and/or the aortic catheter are then both located outside the chest wall of the patient.

A sheath, a coupler and a conical shaped-device are preferably attached at each end of graft 360 (proximal end and distal end). Additionally, the third elongated instrument, e.g., thoracic catheter 305, FIG. 12, preferably with hemostatic object 320 are placed into graft 360. In one example, elongated instrument 300, FIG. 12, illustrates sheath 310, coupler 340 and conical-shaped device 330 at the end of graft 360 closer to the coronary artery.

In a preferred embodiment of the present invention, sheath 310, which prevents appendage 350 of coupler 340 to penetrate graft 360, may be held in its position by inflating hemostatic object 320 such that the tension exerted by hemostatic object 320 against appendage 350 and sheath 310 holds sheath 310 in its position against graft 360.

Coupler 340 can be attached onto graft 360 preferably at the end of graft 360 by means of the appendages 85. In a preferred embodiment, the proximal coupler is placed, followed by placement of the distal coupler and the thoracic catheter. Coupler 340, while it can have any design, preferably has a following design:

The attachment of coupler 340 onto graft 360 can be done by any conventional means such as barbs, or can be sewed onto the graft. The ring is preferably attached to the graft by locking barbs that are tension loaded such that the barbs release upon the tension being removed. The tension is removed by way of withdrawing a retaining sheath, such that the barbs are deployed into the graft wall. The sheath may exist separately from the thoracic catheter, or may extend as a skirt from the conical device. The sheath may be withdrawn or otherwise moved to uncover the appendages prior to or after advancement of the graft onto the guiding devices. The ring of the preferred embodiment is compressed and can be placed in a conical-shaped or other shaped device such as conical-shaped device 330. Conical-shaped device 330 may also include an aperture through the tip of the cone that permits the insertion of the coronary guide device (e.g., perforating guide device). The guide device is preferably threaded through the conical-shaped device and the inner diameter of the graft to provide a navigation path for the graft to the site of the coronary aperture.

The third elongated instrument preferably containing at least one hemostatic object, which holds appendage 350 of coupler 340, sheath 310, and graft 360 in place, can be used to navigate and direct coupler 340 and graft 360 to the coronary aperture site. The third elongated instrument preferably with the hemostatic object 320 is preferably used to stabilize the movement of graft 360 relative to the coronary aperture site. Additionally, as will later be described, the third elongated instrument with preferably the hemostatic object permits the releasing of the flexible ring from the conical-shaped device, which further releases the attached barbs or other connecting means onto the wall surrounding the coronary aperture site.

With the conical-shaped device and the ring properly positioned at the end of the graft, sheath 310 can be withdrawn, exposing appendage 350 of coupler 340. The hemostatic object 320 can then be expanded, driving the barbs or other attachment means of appendage 350 through graft 360. Additionally, the process of driving the barbs can also occur due to passive expansion of these barbs. In one embodiment, an external collar against which the barbs can be driven is added and can serve as an additional hemostatic or biologic functions.

The conical-shaped device is then inserted into the coronary aperture preferably to a point where conical-shaped device passes entirely through the coronary aperture. This is preferably accomplished by a dilator at the end of the conical-shaped device 330. At this point, the hemostatic object or balloon in the interior of the graft remains inflated so the hemostatic object or balloon still presses against the coupler and the graft. An inner-most element of the third elongated instrument which distally is attached to the conical-shaped device can then be pushed forward while the coupler is held in place by holding the hemostatic object in position (the inner-most element of the third elongated instrument can slide relative to the component of the third elongated instrument to which the hemostatic object is attached). This pushing movement of the conical-shaped device, while maintaining the location of the graft, releases the compressed ring from conical-shaped device 330. The releasing of the compressed ring thus permits the now uncompressed ring, with one end attached to the graft, to press against the entire circumference around the coronary aperture. This action further releases and imbeds any attachment means, such as barbs, into the interior wall of the coronary artery surrounding the coronary aperture, and creates a fluid tight connection by transferring the tension exerted by the expanded ring through the distensible arms to the appendages. At this point, a bio-adhesive or other sealing agents can be used to further ensure a fluid tight connection between the graft and the walls surrounding the coronary aperture. In a preferred embodiment, the creation of the aperture by the dilator located at the distal end of conical-shaped device and deployment of the coupler is nearly a continuous process.

At this point, the conical-shaped device, which is preferably collapsible and flexible, can be withdrawn from the coronary artery through the graft and to the exterior of the patient by way of the thoracic aperture. This would also be true for collapsible hemostatic object, and the third elongated instrument.

Figure 13:
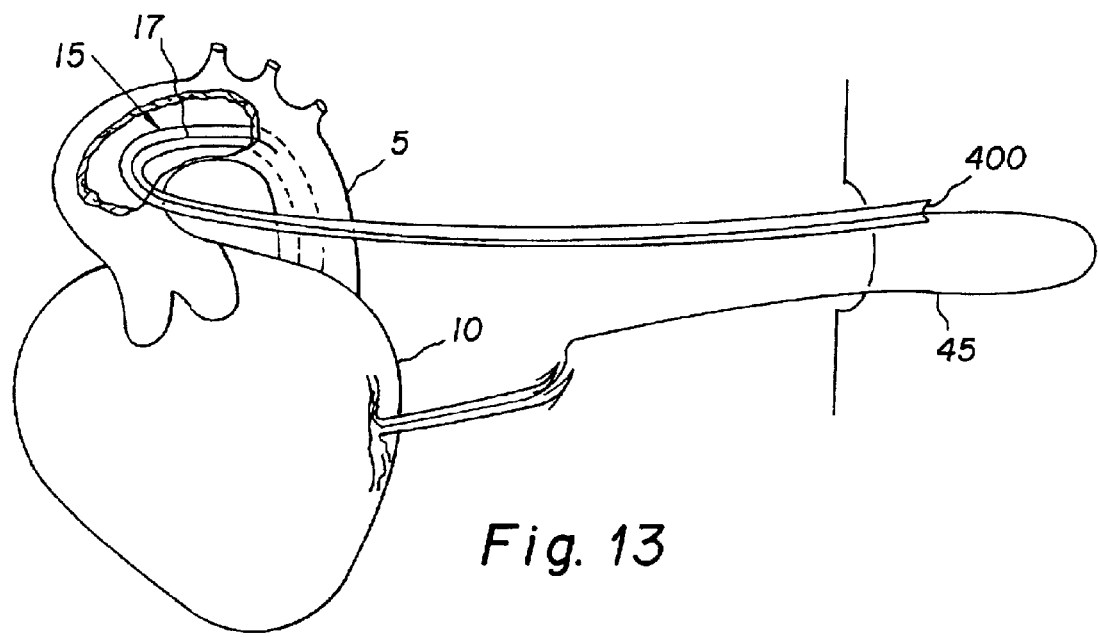
FIG. 13 is a schematic diagram illustrating one method of connecting the aortic catheter to the proximal end of the graft.

As discussed above, using the aortic guide device, the aorta catheter with balloon (e.g., aortic catheter 17 and balloon 400, FIG. 13) can be inserted through the femoral artery of the patient and pass through the aorta and through the aortic aperture and then the thoracic aperture to the exterior of the patient. The distal end of the coronary guide device or the T-shaped perforating guide device can then be inserted into the aorta catheter and fed completely through to the femoral artery or other entry point of the patient such that the distal end of the coronary guide device or the T-shaped perforating guide device is visible at this location. In the alternative, if the length of the graft is long enough to be visible or to be physically outside of the thoracic aperture, the aorta catheter preferably with a balloon can be inserted into the unattached end of the graft without the need to feed the coronary guide device or T-shaped perforating guide device into the aorta catheter. This would be a more simplified approach if it is physically possible due to the length of the graft. Either approach can be used depending upon the circumstances and the length of the graft.

The aortic catheter with balloon is inserted into the proximal (unattached) end of graft such that the balloon engages the coupler at the proximal end of the graft to navigate the proximal end of the graft to the aorta aperture site. As indicated above, the use of the coronary guide wire or T-shaped perforating guide device, with the feeding of this device into the aortic catheter, is for purposes of guiding the aorta catheter preferably with a balloon into the unattached (proximal) end of the graft. Thus, the coronary guide device or T-shaped perforating guide device makes it quite possible to navigate the aortic catheter with balloon into the proximal end of the graft. Upon reaching the site, the aortic catheter with the balloon is withdrawn towards the aorta aperture to a point where the end of the graft is prepared for attachment onto the wall surrounding the aorta aperture. A coupler, such as described earlier, is used at this end of the graft 360 to attach onto the aorta, in a similar manner as the coupler that was used to attach the distal end of the graft now attached to the coronary artery. In other words, a compressed tension loaded ring has been previously attached onto the proximal end of the graft and a device similar to the conical-shaped device is preferably used to keep the releasable ring in a compressed state.

Figure 14:
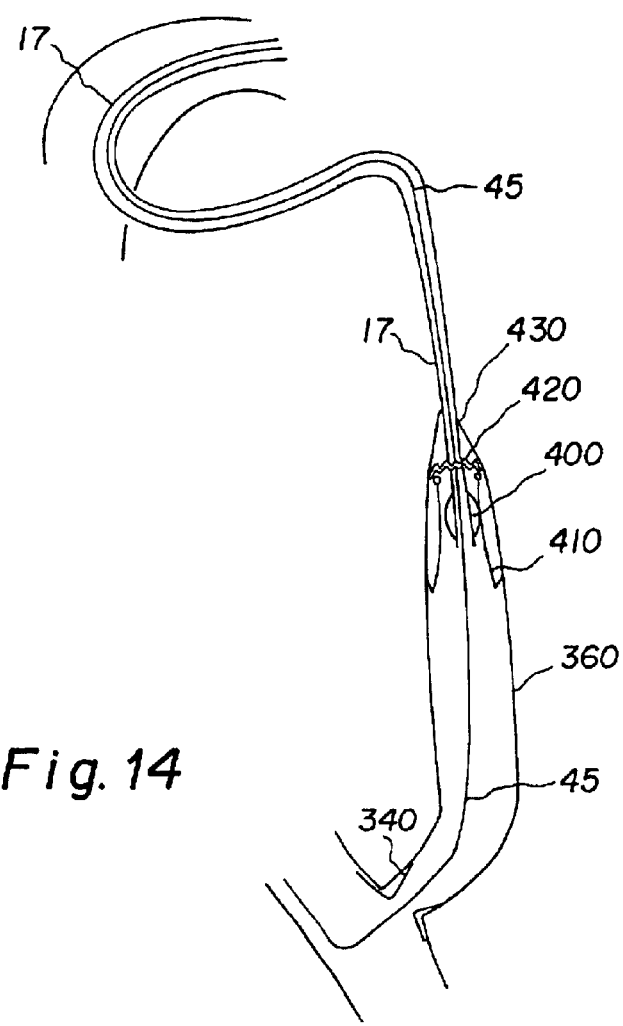
FIG. 14 is a schematic diagram illustrating one method of maneuvering the proximal end of the graft towards the aorta.

The aortic catheter with balloon is preferably inserted through the aperture of the second conical-shaped device. Once the conical-shaped device is holding the compressed ring, the balloon can be expanded to press against the graft and/or coupler, which permits the ability to maneuver and navigate the graft to the aorta aperture. FIG. 14 illustrates an example wherein catheter 17 with balloon 400 is inserted through aperture 430. Additionally, compressed ring 420 is inside the conical-shaped device and balloon 400 is expanded to press against graft 360 and/or coupler 410. Once at the aperture site, and after traction with the balloon on the coupler has caused the conical-shaped device to enter through the aortic aperture, the balloon can be deflated slightly in order to avoid pressing against the graft wall while having a sufficient diameter to press up against the conical-shaped device and to remove the conical-shaped device from the compressed ring. This procedure permits the ring to release to its normal diameter and attach onto the wall surrounding the aorta aperture, and thereby attaching the proximal end of the graft onto the aorta wall. The aortic catheter with balloon and the conical-shaped device can then be retrieved from this area by retracting the coronary guide device (if used) or preferably T-shaped perforating guide device 45 (if used) and aortic catheter with balloon through the original entry point of the femoral artery at the leg site. Again, bio-adhesive or other sealing means can be used to further ensure a fluid tight connection between the graft and the wall surrounding the aorta aperture.

With respect to a bypass conducted on the mammary artery, in this procedure, a thoracic aperture can be created in order to obtain access to the desired mammary artery to be used for the bypass procedure. Then, using conventional surgery techniques, one end of the mammary artery can be cut (using, for instance, a thoracoscope) in order to create a distal end or severed end of the mammary artery. This end of the mammary artery can then be prepared for attachment onto the coronary aperture.

With respect to the bypass procedure using a mammary artery, once the mammary artery is severed to create a severed end of the mammary artery, the mammary guide device is navigated to a point where the mammary guide device exits out of the severed end of the mammary artery and is preferably exited outside of the thoracic aperture to the point where it is visible. Then, a thoracic catheter can be inserted along the mammary guide device such that the thoracic catheter enters the severed end of the mammary artery and is navigated such that the distal end of the thoracic catheter exits out of the entry point where the mammary guide device was originally inserted into the patient. At this point, the distal end of the thoracic catheter is visible at the insertion point of the mammary guide device and the proximal end still preferably is external to the thoracic aperture such that it is visible as well. At this point, the mammary guide device can be withdrawn from the patient.

Also, the coronary guide device can then be navigated such that the distal end of the coronary guide device exits out the thoracic aperture as well. At this point, the distal end of the coronary guide device is visible as well as the proximal end of the thoracic catheter. The distal end of the coronary guide device can be fed through the proximal end of the thoracic catheter and then navigated such that it also exits out of the original insertion point of the mammary guide device in the patient. Once this is accomplished, the proximal end of the thoracic catheter can be navigated such that the proximal end of the thoracic catheter is guided to the severed end of the mammary artery and actually is inserted in the severed end of the mammary artery.

In a preferred embodiment, the proximal end of the thoracic catheter has a hemostatic device or an inflatable balloon and once inserted into the severed end of the mammary artery, can be inflated such that the balloon presses up against the walls of the mammary artery and thus the mammary artery by way of the thoracic catheter can be guided along the coronary guide wire to the coronary aperture. In a preferred embodiment, just as in the above-described bypass procedure, the coronary guide device is fed through a conical-shaped device which holds a compressible coupler that is attached to the severed end of the mammary artery. The coronary guide device, once inserted into and through the coupler, preferably through the conical-shaped device in a preferred embodiment, which also includes inserting through the thoracic catheter, actually exits out of the insertion point of the mammary guide device of the patient.

The thoracic catheter along with the severed end of the mammary artery can then be guided to the coronary artery aperture and coupled to the coronary aperture in the same manner as described above using the same release procedure described above. Afterwards, the various catheters and guide devices can be withdrawn from the original insertion points of the patient.

Thus, the procedure remains the same wherein a mammary guide wire is introduced like the first elongated instrument discussed earlier, through the mammary artery and exited through the thoracic aperture region and, after positioning of a thoracic catheter with a coupler mechanism over the mammary guide wire, the mammary guide wire is removed and the coronary guide device is fed through the end of the thoracic catheter and is used to guide the cut end of the mammary artery to the coronary aperture. The coronary guide device or second elongated instrument is the same as described previously and is introduced in the same way and creates a coronary aperture in the same way as discussed above.

A thoracic catheter is fed through the mammary artery to the point where the thoracic catheter preferably with a balloon is fed through the cut end of the mammary artery such that it enters into the interior of the cut mammary artery to an extent such that the balloon with the thoracic catheter can be expanded in order to press up against the coupler deployed at the distal end of the mammary artery sufficiently to be able to navigate and direct the cut end of the mammary artery to the coronary aperture site. Once at the coronary aperture site, the same coupling as described above and the same procedure used to release the conical-shaped device or other releasing mechanism used with respect to the coronary aperture can be used here as well. After releasing the attachment means, such as the ring, in order to create a fluid tight connection at the coronary aperture, the thoracic catheter preferably with balloon can be withdrawn from the original entry point of the patient as well as the coronary guide device.

For example, and in more detail, an aperture of from about 1 to about 7 millimeters in diameter is created to dissect the mammary artery away from the chest wall and cut one end of the mammary artery in order to create a severed end or distal end of the mammary artery. Preferably, an endoscopic camera is used to help with this procedure. The mammary guide device and/or first elongated instrument, which is preferably the mammary catheter is inserted into the mammary artery prior to transection. At this point, preferably the hemostatic object is inflated to stop any blood flow. The mammary guide device then exits the cut end of the mammary artery. A second elongated instrument, which can be similar to the second elongated instrument discussed previously, passes through any existing blockage. The coronary guide device preferably protrudes through the coronary artery. The coronary guide device and the mammary guide device are retrieved by a retrieving device and extracted through the thoracic aperture by the same procedure and device as previously discussed above.

Once the mammary guide device and the coronary guide device are preferably extracted outside of the patient through the thoracic aperture the mammary guide device can be used to deliver a third elongated instrument to the distal end of the mammary artery. The third elongated instrument is preferably the thoracic catheter. In the preferred embodiment, the coupler is placed at the end of the thoracic catheter. Preferably, the coupler is a compressible ring that is placed inside the conical-shaped device at the end of the catheter. The thoracic catheter is preferably used to deliver the coupler to the distal end of the mammary artery. However, the coupler within the conical-shaped device can also be delivered by mammary artery catheter from inside the patient's vascular system.

The procedure for delivering the distal end of the mammary artery to the coronary artery and attaching the mammary artery to the coronary artery are similar to the previously discussed procedure for delivering and attaching the distal end of the graft to the coronary. More specifically, a thoracic catheter containing the coupler and the conical-shaped device (analogous to the thoracic catheter for use with the saphenous graft) can be passed through the mammary catheter and/or over the mammary guide device in a manner analogous to loading of the distal end of the vein graft. The mammary guide wire can then be removed. The coronary guide wire is then passed through the central lumen of the conical shaped device and the thoracic catheter as previously described. The thoracic catheter can then be positioned fluoroscopically at the distal, transected end of the mammary artery, as previously described, the thoracic catheter balloon is inflated, holding the coupler in position relative to the sheath, and the sheath and/or conical-shaped device can then be advanced, allowing deployment of the graft appendages. The mammary coupler can then be deployed over the coronary guide device as for the saphenous vein distal anastamosis.

Figure 15:
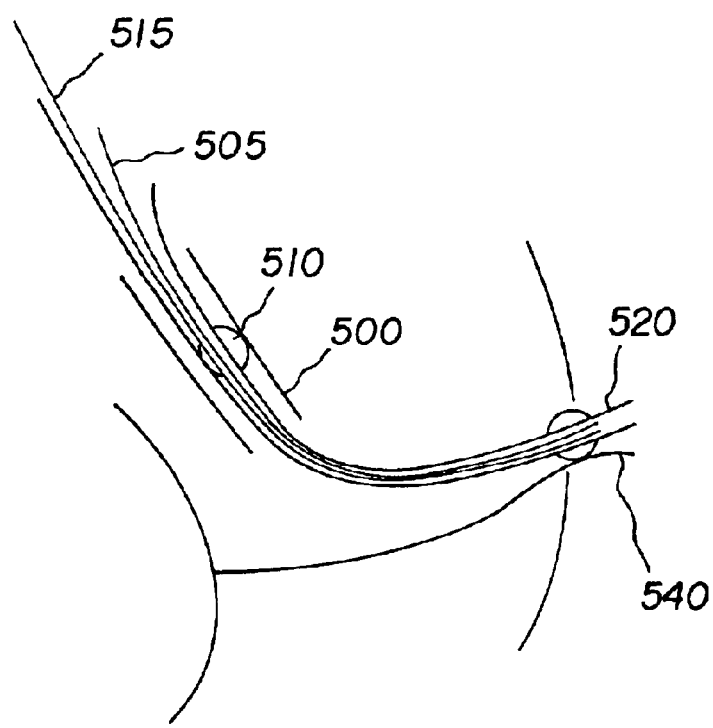
FIG. 15 is a schematic diagram showing the severed mammary artery, the mammary guide wire and the coronary guide wire protruding outside of the patient's thoracic region and the mammary catheter inserted inside the mammary artery.

In one example as shown in FIG. 15, once mammary artery 500 is severed to create a severed end of the mammary artery, mammary guide device 515 is navigated to a point where mammary guide device 515 exits out of the severed end of mammary artery 500 and is preferably exited outside of the thoracic aperture to the point where it is visible. In the preferred embodiment, mammary catheter 505 also includes hemostatic objects 510 to prevent bleeding from the severed end of mammary artery 500. Once mammary guide device 515 is outside of the thoracic aperture, thoracic catheter 520 can be inserted along mammary guide device 515. Also, coronary guide device 540 can be navigated such that the distal end of coronary guide device 540 exits out of the thoracic aperture as well. At this point, the distal end of coronary guide device 540 is visible as well as the proximal end of thoracic catheter 520.

Figure 16:
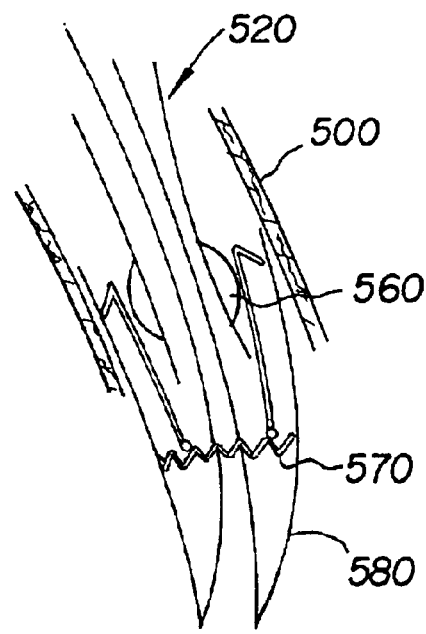
FIG. 16 is a detailed schematic diagram illustrating one example of the coupler and the conical-shaped device at the severed end of the mammary artery.

FIG. 16 illustrates the proximal end of thoracic catheter 520, hemostatic object 560 or an inflatable balloon, coupler 570, and conical-shaped device 580. Once thoracic catheter 520 is inserted into the severed end of mammary artery 500, hemostatic object 560 can be inflated such that balloon presses up against the walls of mammary artery 500.

In FIG. 17, coronary guide device 540 is fed through conical-shaped device 580 which holds coupler 570 that is attached to the severed end of mammary artery 500. Coronary guide device 540 guides coupler 570 and unattached end of mammary artery 500 to coronary artery 585. FIG. 18 illustrates appendages 590 that are deployed and are piercing mammary artery 500. Additionally, in FIG. 18, thoracic catheter 520 along with the severed end of mammary artery 500 are guided to the coronary artery aperture and coupled to the coronary aperture.

The following U.S. patents provide components that can be used in the systems, devices, and methods of the present invention and are incorporated in their entirety by reference herein and form a part of the present application: U.S. Pat. Nos. 6,206,849; 6,165,140; 6,165,139; 6,162,246; 6,157,852; 6,146,355; 6,146,339; 6,083,234; 6,056,719; 6,036,682; 6,340,441; 6,241,667; 6,224,585; 6,214,016; 6,210,312; 5,976,107; 5,957,940; 5,843,028; 5,830,178; 5,718,683; 5,662,675; 5,662,614; 5,575,771; 5,554,139; 5,549,553; 5,484,565; 6,033,378; 6,030,413; 6,027,519; 6,024,748; 6,001,068; and 5,980,484.

As can be seen by the various embodiments, there is preferably no interengaging of guide wires or instruments from each aperture site. In the current medical procedure, the wires or instruments from each aperture site are preferably not connected together or interengaged.

Other embodiments of the present invention will be apparent to those skilled in the art from consideration of the specification and practice of the invention disclosed herein. It is intended that the specification and examples be considered as exemplary only, with a true scope and spirit of the invention being indicated by the following claims and equivalents thereof.

What is claimed is:

1. A graft delivery system for using a mammary artery comprising:
   a first elongated instrument that is insertable into a patient's vascular system, wherein said first elongated instrument comprises a mammary catheter and a mammary guide device capable of navigating said mammary catheter to said patient's mammary artery at a pre-determined location;
   a second elongated instrument that is insertable into said patient's vascular system, wherein said second elongated instrument comprises a coronary catheter and a coronary guide device capable of navigating said coronary catheter to a coronary artery at a pre-determined location;
   a retrieving device capable of retrieving said mammary guide device and said coronary guide device and extracting said mammary guide device and said coronary guide device through a thoracic aperture in said patient;
   wherein one end of said retrieving device is magnetic or electrically charged having an opposite polarity than said mammary guide device, or
   one end of said retrieving device comprises a cone-shaped hollow device, or both;
   wherein said system further comprises a third elongated instrument comprising a thoracic catheter; and
   wherein said thoracic catheter in its diameter further comprises a step-off to limit forward movement of said thoracic catheter.

2. The graft delivery system of claim 1, wherein said first elongated instrument further comprises at least one stabilizer to place and hold said first elongated instrument in a pre-determined location.

3. The graft delivery system of claim 1, wherein said coronary guide device comprises a flexible wire.

4. The graft delivery system of claim 1, further comprising a perforating guide device capable of perforating a coronary artery.

5. The graft delivery system of claim 4, wherein said second elongated instrument further comprises a flange to direct said perforating guide device towards said coronary artery wall to perforate said coronary artery.

6. The graft delivery system of claim 1, wherein said second elongated instrument further comprises at least one radio-opaque marker.

7. The grail delivery system of claim 1, wherein said second elongated instrument further comprises at least a first hemostatic object capable of blocking blood flow.

8. The graft delivery system of claim 7, wherein said first hemostatic object comprises a first channel, wherein said first channel directs said blood flow from one side of said first hemostatic object blocking said blood flow to a second side of said first hemostatic object.

9. The graft delivery system of claim 7, wherein said first hemostatic object comprises a second channel housing a perforating guide device.

10. The graft delivery system of claim 9, wherein said perforating guide device is flexible with a sharp end to perforate said coronary artery.

11. The graft delivery system of claim 7, wherein said first hemostatic object is a balloon.

12. The graft delivery system of claim 7, wherein said second elongated instrument further comprises a second hemostatic object capable of being positioned with respect to said first hemostatic object to form a hemostatic chamber within said coronary artery.

13. The graft delivery system of claim 12, wherein said first and said second hemostatic objects comprise a first channel that extends between said first and said second hemostatic objects and is capable of directing said blood flow from one side of said first hemostatic object blocking said blood flow to a side of said second hemostatic object not facing said first hemostatic object.

14. The graft delivery system of claim 12, wherein said first and said second hemostatic objects are balloons.

15. The graft delivery system of claim 1, wherein the said retrieving device is steerable.

16. The graft delivery system of claim 1, further comprising a fiber optic light/video camera system.

17. The graft delivery system of claim 1, further comprising a coupler and said third elongated instrument is insertable from said exterior of said patient's thoracic region into said patient through said thoracic aperture and is navigated by said mammary guide device, wherein said third elongated instrument is for delivering said coupler to a severed end of said mammary artery.

18. The graft delivery system of claim 17, further comprising a sheath over said coupler.

19. The graft delivery system of claim 17, wherein said coupler comprises a compressible ring that is capable of forming back to its original shape.

20. The graft delivery system of claim 19, wherein said compressible ring is made of Nitinol, stainless steel, titanium, polyimide, super-elastic alloys, or combinations thereof.

21. The graft delivery system of claim 19, wherein said ring is compressed inside a conical-shaped device.

22. The graft delivery system of claim 21, wherein said ring is compressible inside said conical-shaped device at said exterior of said patient's thoracic region.

23. The graft delivery system of claim 19, wherein said compressible ring expands within a lumen of a vessel and conforms to the internal geometry of said vessel.

24. The graft delivery system of claim 1, wherein said first elongated instrument is for delivering a coupler to said severed end of said mammary artery.

25. The graft delivery system of claim 1, wherein said first elongated instrument further comprises at least one hemostatic object.

26. The graft delivery system of claim 1, wherein said mammary guide device is capable of protruding outside of said patient's thoracic region.

27. The graft delivery system of claim 1, wherein said coronary catheter is capable of protruding outside of said patient's thoracic region.

28. The graft delivery system of claim 1, wherein said thoracic catheter in its diameter is shaped so as to evert the end of the graft.

29. The graft delivery system of claim 1, wherein said retrieving device is magnetic at its apical aperture.

30. The graft delivery system of claim 1, wherein said mammary catheter further comprises a hemostatic object.

31. A method for using a mammary artery as a graft using a graft delivery system comprising:
   a first elongated instrument that is insertable into a patient's vascular system, wherein said first elongated instrument comprises a mammary catheter and a mammary guide device capable of navigating said mammary catheter to said patient's mammary artery at a pre-determined location;
   a second elongated instrument that is insertable into said patient's vascular system, wherein said second elongated instrument comprises a coronary catheter and a coronary guide device capable of navigating said coronary catheter to a coronary artery at a pre-determined location; and
   a retrieving device capable of retrieving said mammary guide device and said coronary guide device and extracting said mammary guide device and said coronary guide device through a thoracic aperture in said patient;
   said method comprising:
   a) creating a thoracic aperture;
   b) inserting said mammary guide device into said patient's vascular system;
   c) cutting the mammary artery to create a severed end thereof;
   d) navigating the distal end of said mammary guide device to protrude out of the severed end of said mammary artery;
   e) inserting said second elongated instrument into said patient's vascular system;
   f) navigating said second elongated instrument to a pre-determined location in said coronary artery;
   g) protruding said coronary guide device to the outside of said coronary artery, thereby creating a coronary aperture;
   h) retrieving said mammary guide device and extracting said mammary guide device with said retrieving device and retrieving said coronary guide device and extracting said coronary guide device with said retrieving device and from said thoracic region of said patient to outside of said thoracic region of said patient;
   i) inserting a thoracic elongated instrument into said patient by way of the thoracic aperture and navigating the distal end of the thoracic elongated instrument through the severed end of the mammary artery such that the distal end of the thoracic elongated instrument exits through the insertion point of the mammary guide device;
   j) removing the mammary guide device from the patient and inserting the distal end of the coronary guide device into the proximal end of the thoracic elongated instrument and navigating the distal end of the coronary guide device such that the distal end of the coronary guide device exits out the patient through the insertion point of the mammary guide device of the patient; and
   k) attaching said severed end of said mammary artery to said coronary aperture to make a fluid tight connection.

32. The method of claim 31, further comprising inserting a third elongated instrument through said thoracic aperture, wherein said third elongated instrument delivers a coupler to said severed end of said mammary artery, and said mammary guide device is threaded through said third elongated instrument to provide a navigation path for said third elongated instrument to said severed end of said mammary artery.

33. The method of claim 32, further comprising removing said third elongated instrument after delivering said coupler to said severed end of said mammary artery.

34. The method of claim 32, wherein said coupler at said severed end of said mammary artery is released from within said conical-shaped device by advancing the conical-shaped device relative to the position of the coupler, which is maintained by inflation of a balloon component of said third elongated instrument.

35. The method of claim 32, wherein said coupler is a compressible ring.

36. The method of claim 32, wherein said coupler is compressed within a conical-shaped device outside of thoracic region of said patient, and wherein said conical-shaped device is delivered to said severed end of said mammary artery by said third elongated instrument.

37. The method of claim 36, wherein said conical-shaped device at severed end of said mammary artery includes a dilator to dilate said coronary aperture.

38. The method of claim 32, wherein said third elongated instrument is a thoracic catheter having a coupler wherein said thoracic catheter is used to navigate said coupler to said severed end of said mammary artery.

39. The method of claim 38, wherein said coupler at said severed end of mammary artery is attached to said mammary artery by withdrawing a sheath and expanding a hemostatic object within said thoracic catheter.

40. The graft delivery system of claim 31, wherein said first elongated instrument delivers a coupler to said severed end of said mammary artery.

41. The method of claim 31, further comprising inserting a conical-shaped device in said severed end of said mammary artery, wherein said conical-shaped device includes a coupler.

42. The method of claim 41, further comprising inserting said conical-shaped device, at said severed end of said mammary artery, entirely through said coronary aperture.

43. The method of claim 42, further comprising releasing said coupler at said severed end of said mammary artery from within said conical-shaped device to attach said coronary artery to said severed end of said mammary artery.

44. The method of claim 31, further comprising removing said first elongated instrument after attaching said coronary catheter to said severed end of said mammary artery.

45. The method of claim 31, further comprising removing said second elongated instrument after attaching said severed end of said mammary artery to said coronary artery.

46. The method of claim 31, wherein said mammary catheter further comprises a balloon at one end to hold said severed end of said mammary artery and wherein said mammary catheter and said balloon are attached to said severed end of said mammary artery.

47. The method of claim 31, wherein said mammary catheter is navigated to a pre-determined location in said coronary artery by said coronary guide device.

48. The method of claim 31, wherein said retrieving device is a magnetic, electrically charged, or a cone-shaped hollow device end to retrieve said aortic guide device and said coronary guide device.

49. The method of claim 31, further comprising inserting a fiber optic light/video camera system through said thoracic aperture.

* * * * *

UNITED STATES PATENT AND TRADEMARK OFFICE
CERTIFICATE OF CORRECTION

PATENT NO.    : 6,814,751 B2
DATED         : November 9, 2004
INVENTOR(S)   : Rosengart It is certified that error appears in the above-identified patent and that said Letters Patent is hereby corrected as shown below:

Column 18,
Line 56, change "The graft delivery system" to -- The method --.

Signed and Sealed this

Twenty-ninth Day of March, 2005

JON W. DUDAS
*Director of the United States Patent and Trademark Office*